US011946837B2

(12) United States Patent
Ranjan et al.

(10) Patent No.: US 11,946,837 B2
(45) Date of Patent: Apr. 2, 2024

(54) ELECTROACTIVE ACTUATORS AS SAMPLING PORT VALVES FOR ASPIRATING CONTAMINANT DETECTION

(71) Applicant: Carrier Corporation, Palm Beach Gardens, FL (US)

(72) Inventors: Rajiv Ranjan, South Windsor, CT (US); Suman Dwari, Vernon, CT (US); Peter R. Harris, West Hartford, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 703 days.

(21) Appl. No.: 17/054,427

(22) PCT Filed: May 15, 2019

(86) PCT No.: PCT/US2019/032347
§ 371 (c)(1),
(2) Date: Nov. 10, 2020

(87) PCT Pub. No.: WO2019/222305
PCT Pub. Date: Nov. 21, 2019

(65) Prior Publication Data
US 2021/0063287 A1  Mar. 4, 2021

Related U.S. Application Data

(60) Provisional application No. 62/671,835, filed on May 15, 2018.

(51) Int. Cl.
*G01N 1/26* (2006.01)
*G01N 33/00* (2006.01)
*G08B 17/10* (2006.01)

(52) U.S. Cl.
CPC .......... *G01N 1/26* (2013.01); *G01N 33/0063* (2013.01); *G08B 17/10* (2013.01)

(58) Field of Classification Search
CPC ....... G01N 1/26; G01N 33/0063; G08B 17/10
See application file for complete search history.

(56) References Cited

U.S. PATENT DOCUMENTS 3,765,842 A  10/1973 Purt
4,101,887 A  7/1978 Osborne
(Continued)

FOREIGN PATENT DOCUMENTS

DE         3237021 A1   5/1983
DE    102012112564 B4   1/2017
(Continued)

OTHER PUBLICATIONS

European Office Action; European Application No. 19727258.6; dated Jun. 21, 2022; 17 pages.
International Search Report of the International Searching Authority; International Application No. PCT/US2019/032347; International Filing Date: May 15, 2019; dated Jul. 29, 2019; 6 pages.
(Continued)

*Primary Examiner* — Helen C Kwok
(74) *Attorney, Agent, or Firm* — CANTOR COLBURN LLP

(57) ABSTRACT

A detection system includes a central manifold including a detection chamber, a pipe network including at least one pipe fluidly coupled to the central manifold, a plurality of inlets formed over a length of the at least one pipe and an aspirating mechanism operable to draw a fluid flow at each of the plurality of inlets through the pipe network to the central manifold. A plurality of independently operable flow control devices is associated with the plurality of inlets. At least one of the plurality of flow control devices includes a (Continued)

solid state flexible polymer deformable in response to application of a voltage.

19 Claims, 5 Drawing Sheets

(56) References Cited

U.S. PATENT DOCUMENTS

| | | | |
|---|---|---|---|
| 6,985,081 B2 | 1/2006 | Wagner et al. | |
| 8,065,922 B2 | 11/2011 | Ajay et al. | |
| 9,695,951 B2 | 7/2017 | Rodegheri et al. | |
| 2004/0145484 A1* | 7/2004 | Wagner | G08B 17/10 |
| | | | 73/863.31 |
| 2007/0008157 A1* | 1/2007 | Siemens | G08B 17/10 |
| | | | 340/628 |
| 2011/0087467 A1 | 4/2011 | Linden | |
| 2015/0096389 A1* | 4/2015 | Knox | G08B 17/113 |
| | | | 73/864.34 |
| 2015/0310717 A1* | 10/2015 | Al-Farra | G08B 17/02 |
| | | | 340/628 |
| 2015/0369381 A1* | 12/2015 | Rodegheri | F16K 11/07 |
| | | | 137/625.48 |
| 2016/0223437 A1* | 8/2016 | Ajay | G01N 1/26 |
| 2016/0300466 A1 | 10/2016 | Williamson | |
| 2017/0045415 A1 | 2/2017 | Williamson | |
| 2017/0053527 A1 | 2/2017 | McSheffrey | |
| 2019/0154551 A1* | 5/2019 | Richter | G01N 33/0014 |
| 2020/0217771 A1* | 7/2020 | Boersma | G01N 15/0266 |

FOREIGN PATENT DOCUMENTS

| | | |
|---|---|---|
| GB | 2264865 A | 9/1993 |
| JP | H10143779 A2 | 5/1998 |
| KR | 20110115562 A | 10/2011 |
| KR | 20140028861 A1 | 3/2014 |

OTHER PUBLICATIONS

Marc Hill et al: "Development and Experimental Characterization of a Pneumatic Valve Actuated by a Dielectric Elastomer Membrane", Smart Materials and Structures, IOP Publishing Ltd., Bristol, GB, vol. 26, No. 8, Jul. 11, 2017 (Jul. 11, 2017), p. 85023, XP020318277 ISSN: 0964-1726, DOI: 10.1088/1361-665X/AA746D [retrieved on Jul. 11, 2017].

R Sarban, et al., "Dynamic Electromechanical Modeling of Dielectric Elastomer Actuators With Metallic Electrodes" IEEE/ASME Transactions on Mechatronics Year: 2012, vol. 17, Issue: 5 pp. 1-9.

Written Opinion of the International Searching Authority; International Application No. PCT/US2019/032347; International Filing Date: May 15, 2019; dated Jul. 29, 2019; 10 pages.

* cited by examiner

ELECTROACTIVE ACTUATORS AS SAMPLING PORT VALVES FOR ASPIRATING CONTAMINANT DETECTION

CROSS REFERENCE TO RELATED APPLICATIONS

This application is a National Stage application of PCT/US2019/032347 filed May 15, 2019, which claims priority to U.S. Provisional application 62/671,835 filed May 15, 2018, both of which are incorporated by reference in their entirety herein.

BACKGROUND

Embodiments of this disclosure relate generally to a smoke and/or fire detection system associated with a predetermined space and, more particularly, to localization using an aspirating smoke and/or fire detection system.

Conventional smoke or fire detection systems operate by detecting the presence of smoke or other airborne pollutants. Upon detection of a threshold level of particles, an alarm or other signal, such as a notification signal, may be activated and operation of a fire suppression system may be initiated. Aspirating smoke detection systems typically incorporate a pipe network consisting of one or more pipes with holes or inlets installed at positions where smoke or pre-fire emissions may be collected from a region or environment being monitored. Air is drawn into the pipe network through the inlets and is subsequently directed to a central station for evaluation, such as by a fan located within the central station.

In pipe network detection systems, due to the size of the pipe network, smoke or other pollutants initially enter the pipe network through only a few of the inlets. This smoke mixes with the clean air provided to the pipe from the remainder of the inlets. As a result of this dilution, the smoke detectable within the smoke and air mixture may not exceed the threshold necessary to indicate the existence of a fire and initiate an alarm. Further, in instances where the smoke is sufficient to initiate an alarm, the system is unable to determine the location of the one or more inlets where the smoke is present.

BRIEF DESCRIPTION

Disclosed is a smoke detection system includes a central manifold including a detection chamber, a pipe network including at least one pipe fluidly coupled to the central manifold, a plurality of inlets formed over a length of the at least one pipe and an aspirating mechanism operable to draw a fluid flow at each of the plurality of inlets through the pipe network to the central manifold. A plurality of independently operable flow control devices is associated with the plurality of inlets. At least one of the plurality of flow control devices includes a solid state flexible polymer deformable in response to application of a voltage to the solid state flexible polymer to control one or more characteristics of a fluid flow at the inlet associated with the at least one of the plurality of flow control devices.

In addition to one or more of the features described above, or as an alternative, in further embodiments the at least one flow control device is located upstream from the inlet, and downstream from another inlet of the plurality of inlets in the at least one pipe.

In addition to one or more of the features described above, or as an alternative, in further embodiments at least one the plurality of inlets is formed directly in the at least one pipe.

In addition to one or more of the features described above, or as an alternative, in further embodiments the at least one flow control device is located at the inlet.

In addition to one or more of the features described above, or as an alternative, in further embodiments at least one of the plurality of inlets is offset from the at least one pipe and is arranged in fluid communication with the at least one pipe by a connector.

In addition to one or more of the features described above, or as an alternative, in further embodiments the at least one flow control device is located within at least one of the connector and the pipe.

In addition to one or more of the features described above, or as an alternative, in further embodiments the solid state flexible polymer converts electrical energy into mechanical energy.

In addition to one or more of the features described above, or as an alternative, in further embodiments the solid state flexible polymer comprises an electroactive polymer.

In addition to one or more of the features described above, or as an alternative, in further embodiments the solid state flexible polymer comprises a piezoelectric material.

In addition to one or more of the features described above, or as an alternative, in further embodiments the at least one of the plurality of flow control devices comprising a solid state flexible polymer further comprises an electrode, and wherein the solid state flexible polymer is deformable in response to application of a voltage to the solid state flexible polymer via the electrode.

In addition to one or more of the features described above, or as an alternative, in further embodiments the solid state flexible polymer is expandable in response to application of a voltage via the electrode.

According to another embodiment, a method to identify a location associated with detected particles of a contaminant includes detecting particles of the contaminant within a fluid flow provided to a pipe network from a plurality of inlets formed in the pipe network, deforming at least one flow control device, where deforming the at least one flow control device selectively seals at least a portion of the plurality of inlets, and evaluating the fluid flow provided to the pipe system from at least one open inlet to determine if particles of the contaminant are present at the at least one open inlet.

In addition to one or more of the features described above, or as an alternative, in further embodiments selectively sealing at least a portion of the plurality of inlets comprises selectively sealing all but one of the plurality of inlets.

In addition to one or more of the features described above, or as an alternative, in further embodiments the pipe network comprises a plurality of pipes and selectively sealing at least a portion of the plurality of inlets comprises selectively sealing the plurality of inlets associated with all but one of the plurality of pipes.

In addition to one or more of the features described above, or as an alternative, in further embodiments the at least one flow control device comprises a solid state flexible polymer.

In addition to one or more of the features described above, or as an alternative, in further embodiments deforming at least one flow control device further comprises expanding the solid state flexible polymer.

In addition to one or more of the features described above, or as an alternative, in further embodiments expanding the solid state flexible polymer further comprises supplying an electrical energy from a power supply to an actuator associated with the solid state flexible polymer.

In addition to one or more of the features described above, or as an alternative, in further embodiments deforming at least one flow control device comprises applying a voltage to the at least one flow control device associated with at least one of the plurality of inlets.

In addition to one or more of the features described above, or as an alternative, in further embodiments deforming the at least one flow control device selectively seals the at least one inlet, and further comprising selecting one or more parameters associated with the voltage to achieve a desired deformation of the solid state flexible polymer.

In addition to one or more of the features described above, or as an alternative, in further embodiments deforming the at least one flow control device further comprises applying a voltage to an actuator.

In addition to one or more of the features described above, or as an alternative, in further embodiments the particles detected are smoke particles.

In addition to one or more of the features described above, or as an alternative, in further embodiments detection of smoke particles indicates a fire is present adjacent at least one of the plurality of inlets.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

Figure 1:
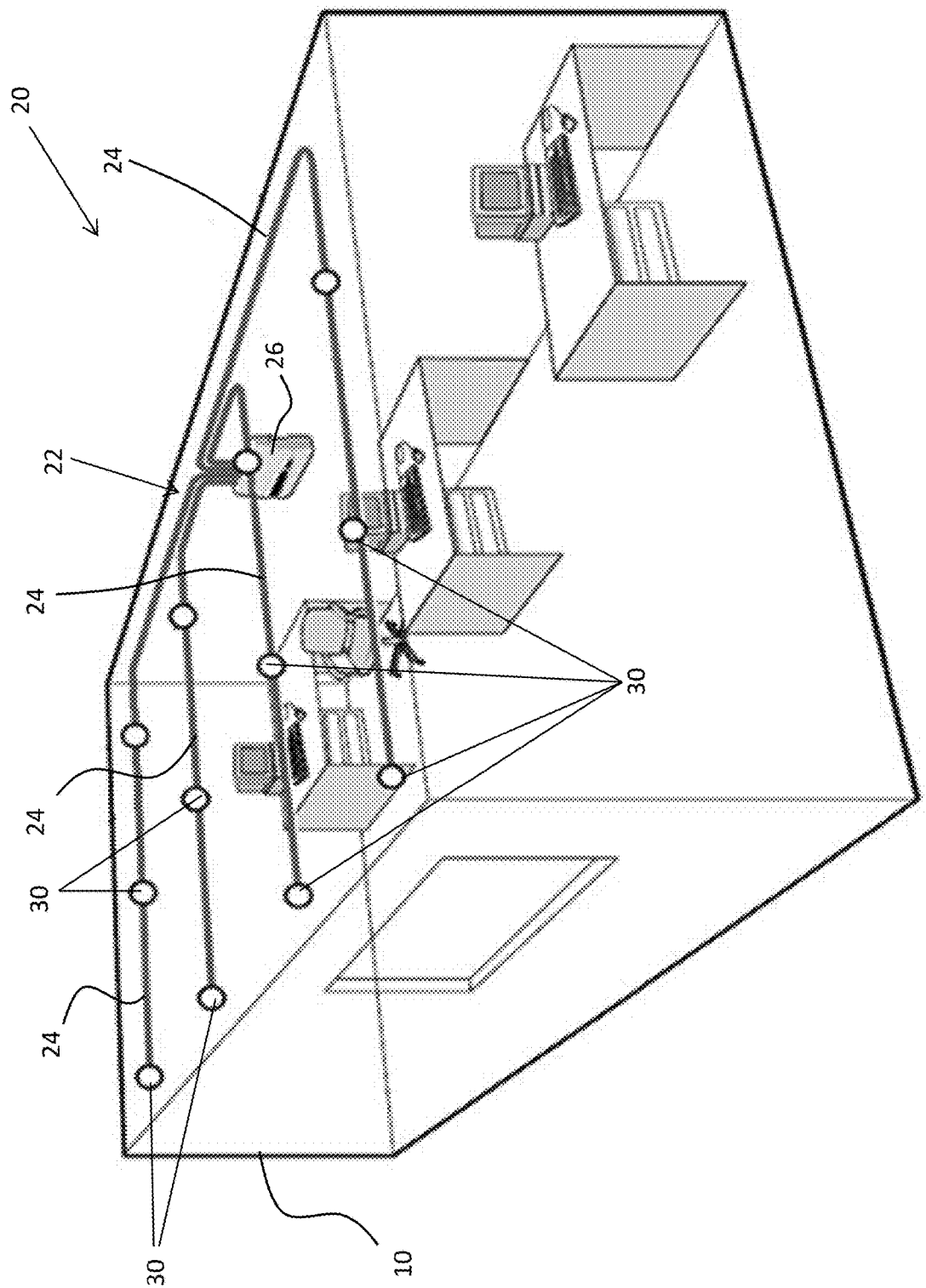
FIG. 1 is a perspective view of an example of an aspirating smoke detection system of a building.

With reference now to FIG. 1, an example of a detection system 20, such as for detecting the presence of smoke or a fire for example, is illustrated. Note that although smoke is typically detected by a detection system 20 and is used illustratively for exemplary embodiments herein, the system 20 may be configured to detect other types of air-borne contaminants or particulates, such as pollen or chemicals, which are likely to indicate a hazardous or undesirable condition or event. As shown, the detection system 20 includes a pipe network 22 having one or more sampling pipes 24 connected to a common or central manifold 26. In the illustrated, non-limiting embodiment, the pipe network 22 includes four distinct pipes 24; however, it should be understood that a network 22 having any number of pipes 24 is considered within the scope of the disclosure. Each sampling pipe 24 is positioned within a specific zone or region of an area, building, or other facility 10, to be monitored by the detection system 20.

Figure 2:
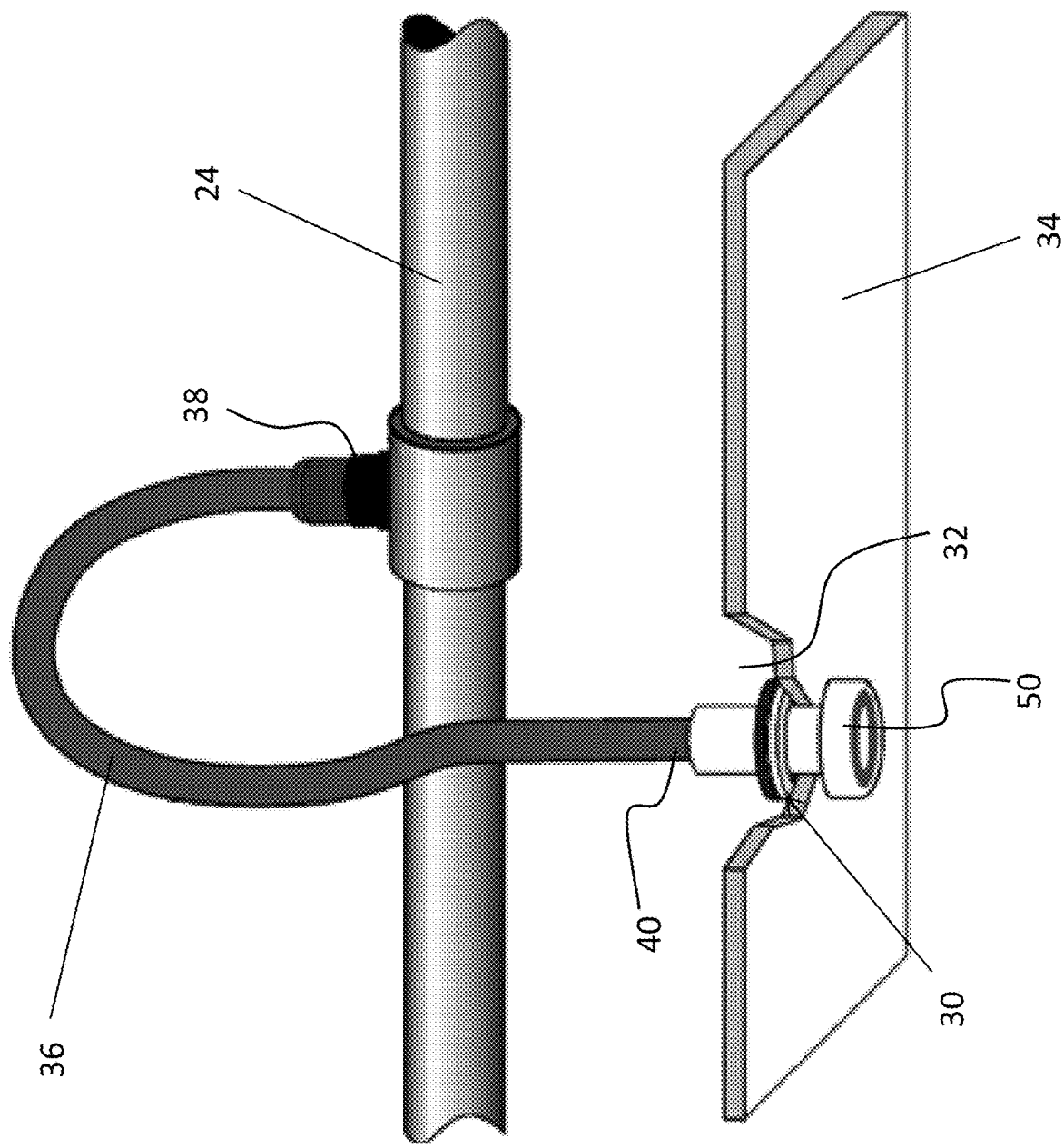
FIG. 2 is an example of an inlet arranged at a location offset from a pipe of the pipe network of a detection system.
Figure 3:
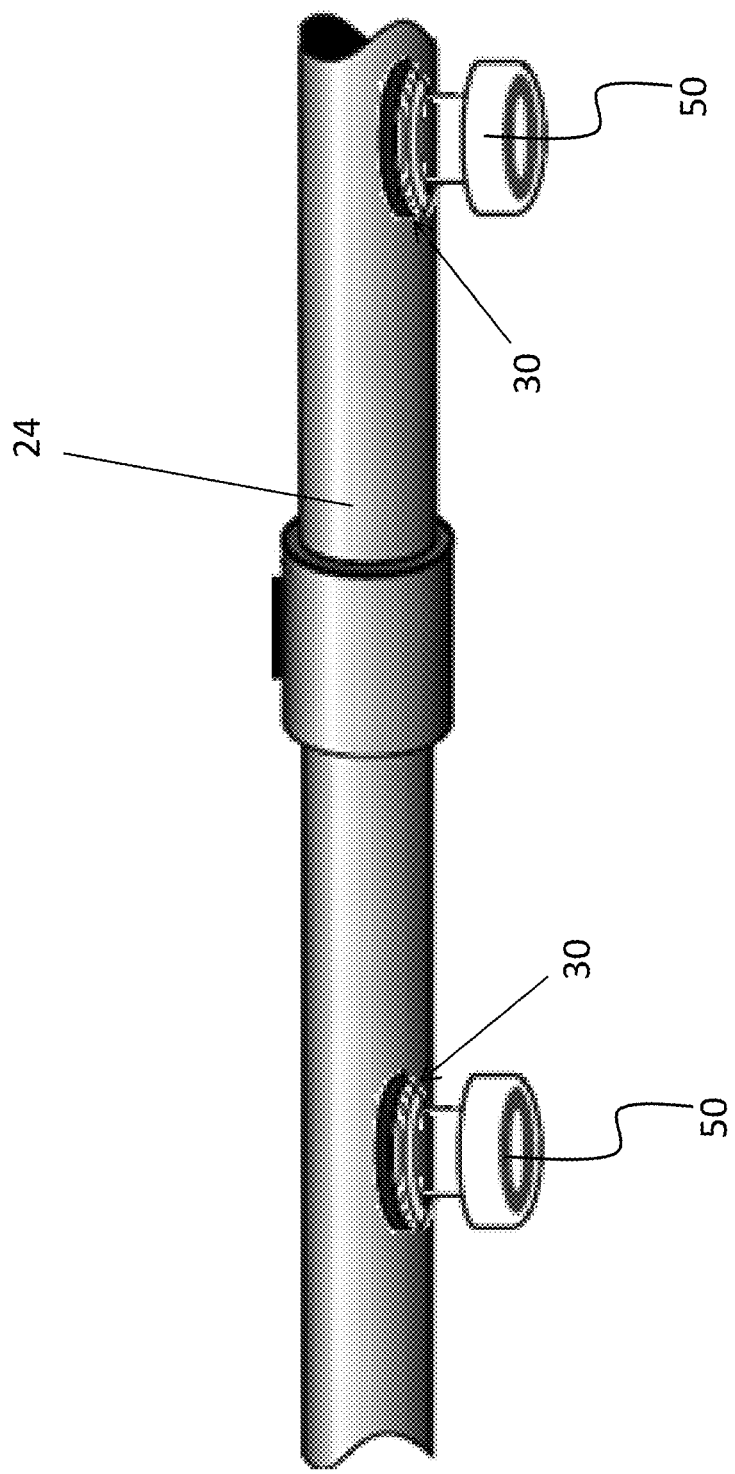
FIG. 3 is an example of an inlet formed directly in a pipe of the pipe network of a detection system.

In addition, each sampling pipe 24 includes one or more sampling inlets or ports 30 disposed at selected positions or intervals over the length of the pipe 24. In some embodiments, such as where the detection system 20 is installed in a building 10 having a drop ceiling, the inlets or ports 30 are located separate or offset from the pipe 24. As best shown in FIG. 2, the inlet or port 30 may extend through an opening 32 formed in a ceiling 34 of the building 10 to fluidly couple the inlet 30 with a portion of the building 10 to be monitored. A connector 36, such as formed by a flexible cable, capillary tube, or other conduit, may communicate the air and particles received at the inlet 30 to the pipe 24. In the illustrated, non-limiting embodiment, a first end 38 of the connector 26 is coupled to an opening (not shown) formed in a pipe 24 of the pipe network 22. A second, opposite end 40 of the connector 36 is coupled to and configured to receive the flow of fluid received at the inlet 30. In another embodiment, illustrated in FIG. 3, the inlet 30 is formed directly into a pipe 24 of the pipe network 22 for communication of air and other particles to the central manifold 26. It should be understood that a system 20 including a combination of one or more inlets 30 formed directly into the pipes 24 of the pipe network 22 and one or more inlets 30 offset from the pipes 24 of the pipe network 22 are also contemplated herein. Further, any other suitable configuration of the inlets 30 relative to the pipe network 22 is also within the scope of the disclosure.

Figure 4:
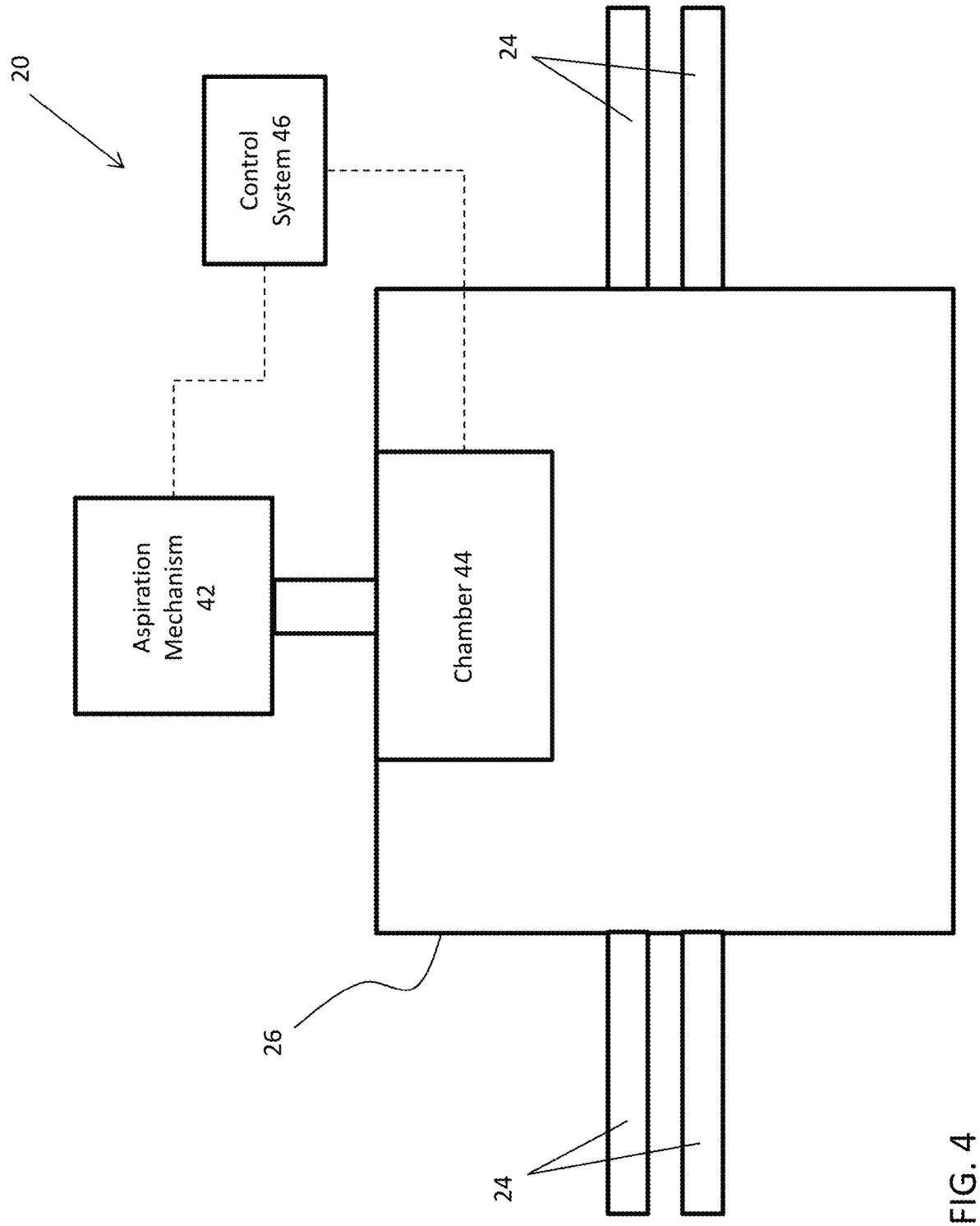
FIG. 4 is a schematic diagram of a central manifold of the detection system according to an embodiment.

With reference now to FIG. 4, a schematic diagram of the central manifold 26 is illustrated. As shown, the central manifold 26 is fluidly coupled to a fan or other aspiration mechanism, illustrated schematically at 42, which draws a flow of air and other particles through the plurality of inlets 30, through the pipes 24, and into the central manifold 26. From the aspiration mechanism 42, the flow may be discharged directly to ambient, i.e. outside the area being monitored, or to an exhaust pipe. Arranged within the central manifold 26 is a chamber 44, within which, prior to being exhausted, all or a portion of the flow of air and other particles provided to the central manifold 26 is sampled to detect the presence of smoke, thereby indicating the occurrence of a fire. A control system, illustrated schematically at 46, is operably coupled to both the aspiration mechanism 42, and to one or more components arranged within the chamber 44 that perform the detection operation. It should be understood that the aspirating detection system 20 illustrated and described herein is intended as an example only, and that other suitable detection systems, such as fiber optic detection systems for example, are also within the scope of the disclosure.

Referring again to FIGS. 2 and 3, a flow control device 50, such as a valve for example, may be associated with one or more of the plurality of inlets 30 of the pipe network 22. In an embodiment, a distinct flow control device 50 is associated with each of the plurality of inlets 30 of the pipe network 22 and is operable to adjust or control one or more characteristics of a flow at the inlet 30. The flow control devices 50 may be located at the inlet 30, or alternatively, within the pipe 24 or connector 36 at a position upstream from the inlet 30, but downstream from an adjacent inlet 30. As described herein a connector located upstream from the inlet 30, but downstream from an adjacent inlet, would be located within the pipe 24 generally between adjacent inlets relative to a flow of fluid through the pipe 24. In an embodiment, the flow control device 50 includes an electroactive polymer, piezoelectric material, a solid state flexible material, or any other material capable of converting between electrical energy and mechanical energy. An electroactive polymer typically includes a polymer that acts as an insulating dielectric between electrodes and is configured to deflect in response to application of a voltage different between the electrodes. As used herein, the term deflection may refer to any displacement, expansion, contraction, torsion, linear or area strain, or any other deformation of a portion of the material.

Figure 5:
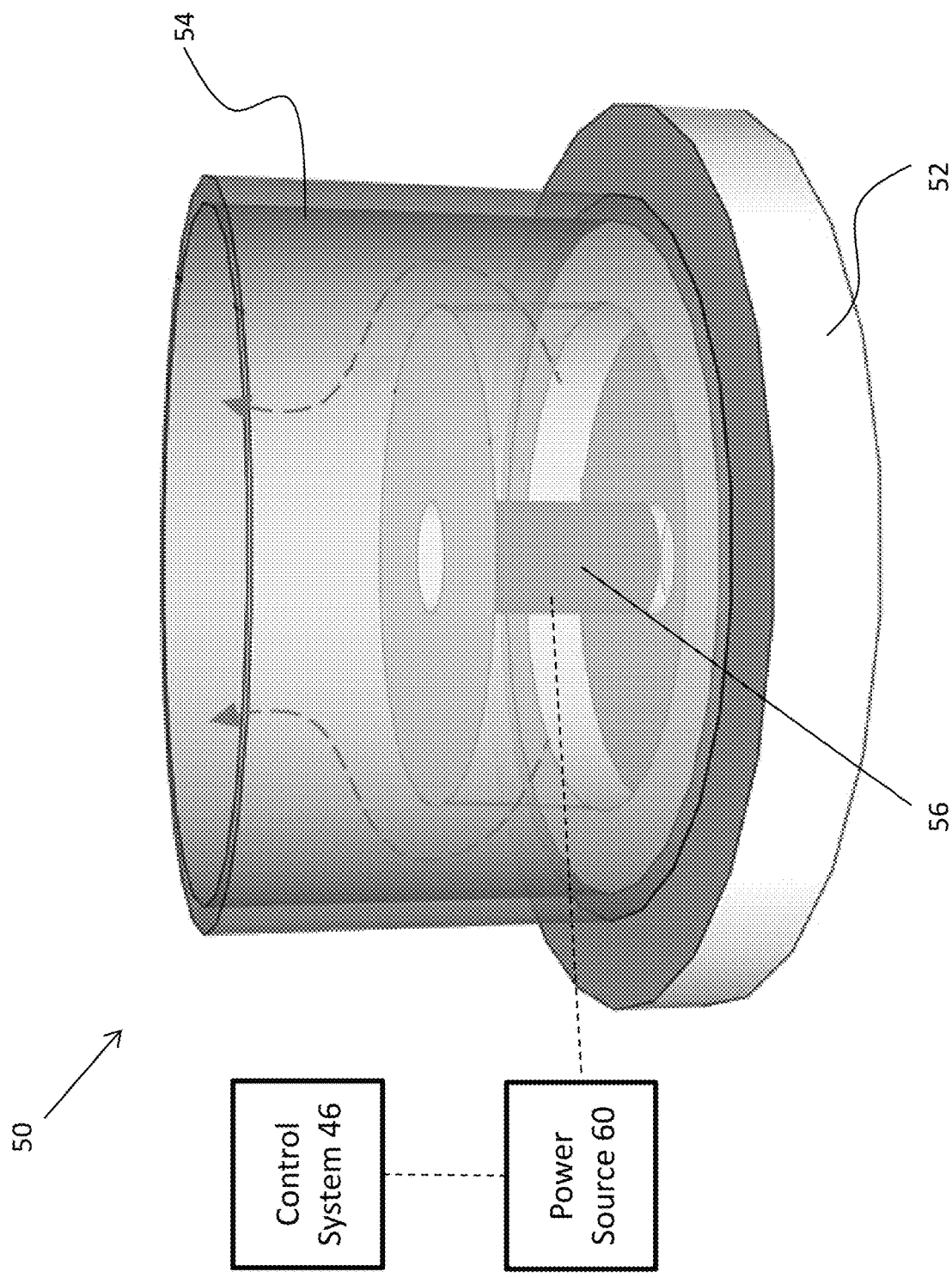
FIG. 5 is a perspective view of a flow control device associated with an inlet of a pipe network of a detection system according to an embodiment.

With reference now to FIG. 5, an example of a flow control device 50 according to an embodiment is illustrated in more detail. As shown, the flow control device 50 includes a base 52 and a sealing element 54 extending from the base 52. The flow control device 50 may be mounted relative to the inlet 30 such that during normal operation, a clearance is defined between the outer periphery of the sealing element 54 and the inlet 30, through which a flow of air and other particles is provided to the pipe network 22. In the illustrated, non-limiting embodiment, the sealing element 54 is formed from an electroactive polymer.

An actuator 56 may be connected to the base 52, such as within a center defined by the sealing element 54. The actuator 56 may be operated to apply a voltage to the electrodes coupled to the electroactive polymer, thereby causing the electroactive polymer of the sealing element 54 to deflect in a desired manner. In the illustrated, non-limiting embodiment, the sealing element 54 is configured to expand such that the outer periphery of the sealing element 54 directly contacts the inlet 30, thereby sealing the inlet 30 to prevent a flow of air there through into the pipe network 22. It should be understood that the flow control device 50, illustrated and described herein is intended as an example only. In other embodiments, the flow control device 50 may include multiple electroactive polymer materials, movable together in response to an electrical charge to selectively seal an inlet of the pipe 24, or alternatively, may include a conventional flow control device such as a valve or cover, that is movable between a plurality of positions relative to the inlet by an actuator. In such embodiments, the actuator may be formed from an electroactive polymer material or another electrically responsive material.

As previously described, the electroactive polymer, piezoelectric material, or other suitable material requires application of an electrical energy or voltage thereto, which is converted into a mechanical energy. In an embodiment, this electrical energy may be supplied from a power source, illustrated schematically at 60 in FIG. 5, such as a battery or another replaceable or rechargeable power source. Alternatively, or in addition, the flow control device 50 may be configured to harvest energy or receive wirelessly transferred power which may then be stored within the coupled power source 60. As shown in the FIG., the power source 60 is operably coupled to the control unit 46 of the detection system 20. The communication between the control system 46 and each of the plurality of flow control devices 50, or a power source associated with each of the plurality of flow control devices 50, may be wired or wireless. Accordingly, the control unit 46 may communicate with the power source 60 to indicate when energy is to be supplied from the power source 60 to flow control device 50, as well as one or more parameters of the associated with the energy to be supplied, to achieve a desired deflection of the electroactive polymer material. In an embodiment, electrical energy is provided to one or more flow control devices 50 at a frequency having a bandwidth between 0.1 and 100 Hz. However, embodiments where the electrical energy is outside of this range, such as greater than 1 KHz for example, are also within the scope of the disclosure.

During normal operation of the detection system 20, all or a plurality of flow control devices 50 are in an open configuration such that a flow of air and other particles is provided to the pipe network 22 through the plurality of corresponding inlets 30. Accordingly, the flow from each of the plurality of "open" inlets 30 mixes within the pipe network 22 and within the manifold 26. This mixture is provided to the detection chamber 44 where the flow is evaluated for the presence of one or more specific particles, such as smoke for example. When smoke or other airborne contaminant or particulate exceeding a predetermined threshold are detected within the flow, the control unit 46 indicates the occurrence of an event. However, the control unit 46 of the detection system 20 is unable to identify the location of the one or more inlets 30 where the smoke originated due to the mixing that occurs within the pipe system 22.

To perform a localization operation and determine the one or more inlets 30 through which smoke is entering the pipe network 22, the control unit 46 will selectively operate the plurality of flow control devices 50 in a controlled manner. In an embodiment, the control unit 46 will seal all but one of the inlets 30 that were open when the smoke was initially detected. The control unit 46 will then open each of the potential inlets 30 through which smoke may have entered the pipe network 22 individually, to identify which of the inlets 30 is the source of the smoke. Alternatively, or in addition, to reduce time and eliminate the need to individually test a flow at each of the inlets 30 of the system 20, the control unit 46 may be operable to selectively seal the flow control devices 50 associated with one or more groups of inlets 30, for example by isolating each pipe 24 from the remainder of the network 22. The modes of operation described herein are intended as an example only, and it should be understood that a detection system operable to selectively seal one or more ports to determine a location associated with the presence of one or more smoke particles is contemplated herein.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A detection system comprising:
a central manifold comprising a detection chamber;
a pipe network comprising at least one pipe fluidly coupled to the central manifold;
a plurality of inlets formed over a length of the at least one pipe;
an aspirating mechanism operable to draw a fluid flow at each of the plurality of inlets through the pipe network to the central manifold; and
a plurality of independently operable flow control devices associated with the plurality of inlets, at least one of the plurality of flow control devices includes:
a base;
an actuator connected to the base; and
a sealing element formed from a solid state flexible polymer deformable in response to application of a voltage, wherein the sealing element is configured to expand in response to the application of the voltage such that an outer periphery of the sealing element directly contacts an inlet of the plurality of inlets to seal the inlet.

2. The detection system of claim 1, wherein the at least one flow control device is located upstream from an inlet of the plurality of inlets, and downstream from another inlet of the plurality of inlets in the at least one pipe.

3. The detection system of claim 1, wherein at least one of the plurality of inlets is formed directly in the at least one pipe.

4. The detection system of claim 3, wherein the at least one flow control device is located at the inlet.

5. The detection system of claim 1, wherein at least one of the plurality of inlets is offset from the at least one pipe and is arranged in fluid communication with the at least one pipe by a connector.

6. The detection system of claim 5, wherein the at least one flow control device is located within at least one of the connector and the pipe.

7. The detection system of claim 1, wherein the solid state flexible polymer converts electrical energy into mechanical energy.

8. The detection system of claim 7, wherein the solid state flexible polymer comprises an electroactive polymer.

9. The detection system of claim 7, wherein the solid state flexible polymer comprises a piezoelectric material.

10. The detection system of claim 1, wherein the at least one of the plurality of flow control devices comprising the solid state flexible polymer further comprises an electrode, and wherein the solid state flexible polymer is deformable in response to application of a voltage to the solid state flexible polymer via the electrode.

11. The detection system of claim 10, wherein the solid state flexible polymer is expandable in response to application of the voltage via the electrode.

12. A method to identify a location associated with detected particles of a contaminant, the method comprising:
providing at least one flow control device associated with a plurality of inlets of a pipe network, the at least one flow control device including a base, an actuator connected to the base, and a sealing element formed from a solid state flexible polymer deformable in response to application of a voltage, the sealing element being configured to expand in response to the application of the voltage such that an outer periphery of the sealing element directly contacts an inlet of the plurality of inlets to seal the inlet;
detecting particles of the contaminant within a fluid flow provided to the pipe network from the plurality of inlets formed in the pipe network;
deforming at least one flow control device, where the deforming at least one flow control device selectively seals at least a portion of the plurality of inlets; and
evaluating the fluid flow provided to the pipe network from at least one open inlet to determine if particles of the contaminant are present at the at least one open inlet.

13. The method of claim 12, wherein the selectively sealing at least a portion of the plurality of inlets comprises selectively sealing all but one of the plurality of inlets.

14. The method of claim 12, wherein the pipe network comprises a plurality of pipes and the selectively sealing at least a portion of the plurality of inlets comprises selectively sealing the plurality of inlets associated with all but one of the plurality of pipes.

15. The method of claim 12, wherein the expanding the solid state flexible polymer further comprises supplying an electrical energy from a power supply to an actuator associated with the solid state flexible polymer.

16. The method of claim 12, wherein the deforming the at least one flow control device selectively seals the at least one inlet, and further comprising selecting one or more parameters associated with the voltage to achieve a desired deformation of the solid state flexible polymer.

17. The method of claim 12, wherein the deforming the at least one flow control device further comprises applying a voltage to an actuator.

18. The method of claim 12, wherein the particles detected are smoke particles.

19. The method of claim 18, wherein detection of the smoke particles indicates a fire is present adjacent at least one of the plurality of inlets.

* * * * *